United States Patent [19]

Hu et al.

[11] Patent Number: 5,412,997
[45] Date of Patent: May 9, 1995

[54] NONDESTRUCTIVE TESTING APPARATUS AND METHOD

[75] Inventors: Dyi-Chung Hu, Shuang-Shi; Jen-Huang Jeng, Chien-Kung, both of Taiwan, Prov. of China

[73] Assignee: Industrial Technology Research Institute, Hsinchu, Taiwan, Prov. of China

[21] Appl. No.: 989,603

[22] Filed: Dec. 11, 1992

[51] Int. Cl.[6] .................. G01N 19/04; G01N 3/08
[52] U.S. Cl. ..................... 73/827; 73/150 A; 73/821
[58] Field of Search .......... 73/150 A, 827, 821

[56] References Cited

U.S. PATENT DOCUMENTS

| | | | |
|---|---|---|---|
| 3,564,911 | 2/1971 | Slemmons et al. | 73/150 A |
| 3,945,248 | 3/1976 | West | 73/827 |
| 4,282,758 | 8/1981 | Wootten et al. | 73/827 |
| 4,413,510 | 11/1983 | McCusker et al. | 73/150 A |
| 4,586,371 | 5/1986 | Ivie et al. | 73/150 A |
| 4,856,326 | 8/1989 | Tsukamoto | 73/150 A |
| 4,934,185 | 6/1990 | Nishiyama et al. | 73/150 A |
| 5,027,650 | 7/1991 | Oblas et al. | 73/150 A |
| 5,085,084 | 2/1992 | Salatino | 73/827 |
| 5,214,963 | 6/1993 | Widder | 73/827 |

FOREIGN PATENT DOCUMENTS 0060683  5/1977  Japan .................. 73/150 A

Primary Examiner—Diego F. F. Gutierrez
Attorney, Agent, or Firm—Bo-In Lin

[57] ABSTRACT

The present invention comprises a test system for nondestructively testing the attachment strength of a plurality of electric wires each connected to a corresponding input/output (I/O) port in an integrated circuit (IC) dice. The test system comprises a test bench for placing said integrated circuit dice thereon. The test system further comprises a force asserting means including a testing pin for asserting a controlled amount of pressing force along a predefined direction to each of the electric wires near said corresponding I/O ports on said IC dice. The test system also includes a control means including a testing arm connecting to the testing pin for controlling and positioning the testing pin to apply the controlled amount of force to each of the electric wires. The control means further includes a force measurement means for measuring the amount of force applied to each of the electric wires. The control means further comprising a positioning means which includes a plurality of stepping motors for adjusting the position of the testing arm. A test computer is connected to the control means to control the control means whereby the testing processes are performed in an automated manner.

13 Claims, 4 Drawing Sheets

NONDESTRUCTIVE TESTING APPARATUS AND METHOD

BACKGROUND OF THE INVENTION

1. Field of the Invention

This invention relates generally to an apparatus and method for non-destructively testing the bonding strength of the connection lines to the circuits on an integrated circuit (IC) chip. More particularly, this invention relates to the apparatus and method for non-destructively testing the bonding strength of the connection lines to the circuits on an IC chip wherein the bonding is formed by utilizing a tape automatic bonding (TAB) machine.

2. Description of the Prior Art

The reliability of the electrical connections wherein the external lines are to be securely attached to the integrated circuits (ICs) on an IC chip may often become a quality issue after a period of field operation. The main reason of this concern is caused by the fact that an effective nondestructive testing apparatus and method to determine the bonding strength of these connections are still not available.

One of the techniques for bonding the external lines to the ICs is tape automatic bonding (TAB) which uses a hot thermode to gang bond the electrical connections. Unlike wire bonding, gang bonding offers the advantage of making many bonds in a single action. Since a higher density interconnection can be achieved by TAB, it becomes popular as the inputs/outputs (I/O's) of the IC die continue to increase while the pitches between the pads are decreased. Because TAB provides greater bond strength, it offers additional advantage that a better reliability is generally achievable by applying TAB in IC manufacturing than the wire bonding.

Since many bonds are formed in a single operation by applying the gang bonding technique, an operational error or a processing parameter deviation may result in defective bonds in that operation. For that reason, more precise control has to be exercised to increase the product yield of the gang bonding process and to assure that the quality of these bonds satisfies the reliability requirements.

Defective bonds may often occur during the gang bonding process due to the temperature variations of the thermode which is frequently caused by the lack of planarity or improper design of the thermode. The bonds formed under non uniform temperature may often lack sufficient bond strength. It may also result in variations in bond height which will cause insufficient contact between the leads and the bump formed by the gang bonding process. Many weak or defective bonds may be formed by the gang bonding process which will adversely affect the reliability and performance of the final products produced by such processes if not properly tested and then rejected or corrected.

The weak bonds caused by the aforementioned problems often cause the bond strength to be less than a pull strength requirement which is approximately 10 grams. Although the pull strength formed by the gang bonding process may not be sufficient for regular field operation, the defects can not be detected by routine open-loop/close-loop electrical testing. The weak bonds however may cause reliability problems since poor lead connection may result due to the failure of these bonds during regular installation, transportation or other types of operational processes.

In order to assure that the TAB bonding formed between the electric wires and the I/O ports on an IC dice have sufficient attachment strength, a destructive test, as shown in FIG. 1, is performed. An electric lead 2 is attached to an IC dice 3 wherein the attachment is established by utilizing a TAB carrier tape 4 to form a TAB bump 5 between the electric wire 2 and the IC dice 3. A testing hook 6 is used to perform a pull-strength test to the bonding by pulling the electric wire 2 away from the IC dice 3. The usefulness of such a test is very limited for several reasons. First, the process in placing the testing hook underneath each electric wire is very time consuming. There is very limited working space around the leads on the edge for placing the testing hook underneath the leads to conduct the pull-strength test. It is virtually impossible to perform the test on the inner leads because a neighboring lead may often be destroyed in placing the testing hook underneath a lead since the distance between two neighboring leads is so small. Additionally, it is also difficult to precisely control the pulling force and to place the testing hook precisely near the attachment point. The electric wire 2 may often be destroyed without being able to obtain an accurate measurement of the attachment strength between the electric wire 2 and the IC dice 3.

Several nondestructive testing methods are proposed. The first one is to use the X-ray to detect the defective lead/bond interfaces by transmitting X-ray through these interface areas. The X-ray images of these interfaces are inspected to determine if there are non-uniform interface images which may identify the defective bonding. However, since there is no definitive and quantitative correlation between the image abnormality and the bond strength, the results obtained from the X-ray method is not very useful for systematically controlling the quality of the bonding process. Additionally, since the X-ray imaging method is very expensive and time consuming, it is not generally used for nondestructive test. The second method is to apply an ultra-sonic imaging system to obtain an ultra-sonic image of the bonding interfaces. Similarly, the defective interfaces are detected by inspecting the image to determine if a non-uniformity of the image exists in the lead/bond interface. The ultra-sonic imaging method suffers the same difficulties and limitations as the X-ray method. Additionally, a testing sample is to be immersed in the water before the ultra-sonic method is applied. It may cause a corrosion problem which may further adversely affect the reliability of the IC devices produced by this method.

Other than the destructive test by pulling the connection lines, a practical nondestructive test is not available at the present time. Long term reliability of the products can not be properly controlled due to this inability to properly test the bonding strength of these connections.

There is still a need for those skilled in the art to develop an effective nondestructive test to assure that the bonding strength of the external line connections attaching to the ICs are in compliance with the design and operation requirements.

SUMMARY OF THE PRESENT INVENTION

It is therefore an object of the present invention to provide a nondestructive testing apparatus and method to overcome these prior limitations.

Another object of the present invention is to provide an apparatus and method for non-destructively testing the bonding strength of the connection lines to the circuits on an IC chip wherein a test pin is applied directly to the inner leads whereby precise measurements may be obtained.

Another object of the present invention is to provide an apparatus and method such that a nondestructive test of the bonding strength on an IC chip may be controlled by a computer and the testing process may be automated.

Briefly, in a preferred embodiment, the present invention comprises a nondestructive testing apparatus for non-destructively testing the attachment strength of a first object attached to a second object at an attachment point which includes a force asserting means for asserting a controlled amount of force along a predefined direction to the first object near said attachment point. The apparatus further includes a control means for controlling the force asserting means to apply the controlled amount of force near the attachment point.

In one of the preferred embodiments, the present invention comprises a test system for non-destructively testing the attachment strength of a plurality of electric wires each connected to a corresponding input/output (I/O) port in an integrated circuit (IC) dice. The test system comprises a test bench for placing said integrated circuit dice thereon. The test system further comprises a force asserting means including a fine elongated straight test pin for asserting a controlled amount of force along a predefined direction to each of the electric wires near said corresponding I/O ports on said IC dice. The test system also includes a control means including a testing arm connecting to the testing pin for controlling and positioning the testing pin to apply the controlled amount of force to each of the electric wires. The control means further includes a force measurement means for measuring the amount of force applied to each of the electric wires. The control means further comprise a positioning means which includes a plurality of stepping motors for adjusting the position of the testing arm. A test computer is connected to the control means to control the control means whereby the testing processes are performed in an automated manner.

One advantage of the present invention is that it provides an apparatus and method for non-destructively testing the bonding strength on an IC chip.

Another advantage of the present invention is that it provides an apparatus and method for non-destructively testing the bonding strength of the connection lines to the circuits on an IC chip wherein a test pin is applied directly to the connection lines near the attachment point whereby precise measurements may be obtained.

Another advantage of the present invention is that it provides an apparatus and method such that a nondestructive test of the bonding strength on an IC chip may be controlled by a computer and the testing process may be automated.

These and other objects and advantages of the present invention will no doubt become obvious to those of ordinary skill in the art after having read the following detailed description of the preferred embodiment which is illustrated in the various drawing figures.

DETAILED DESCRIPTION OF THE PREFERRED EMBODIMENT

Figure 1:
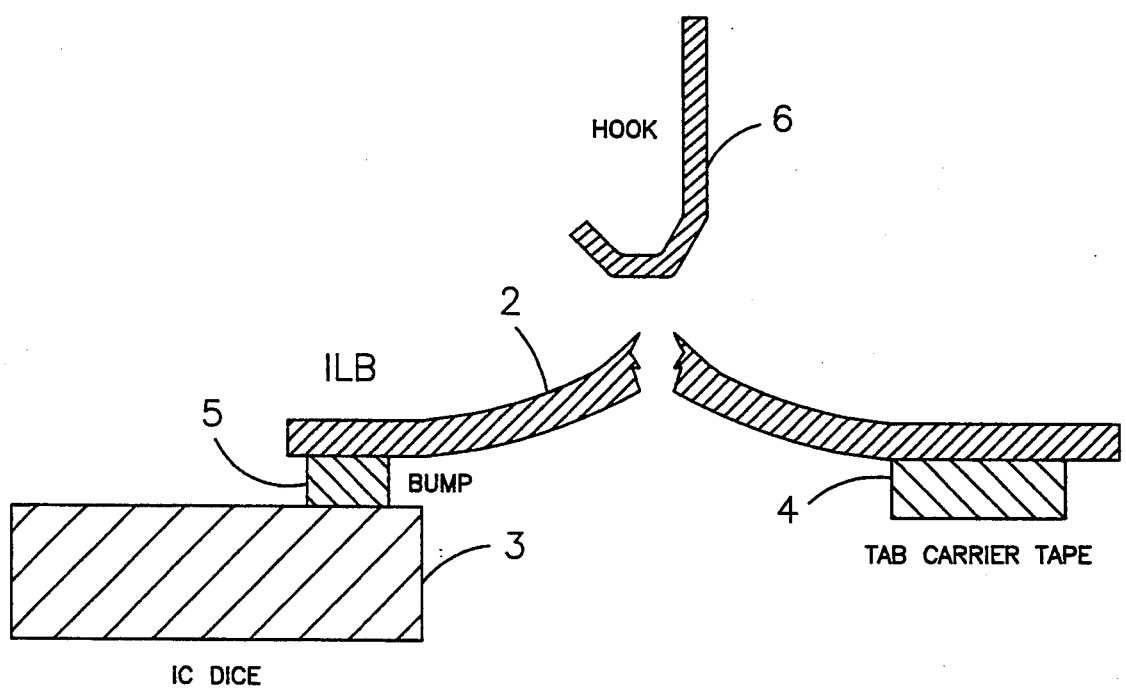
FIG. 1 is diagram showing the process of a pull-test performed on a TAB connection line.
Figure 2:
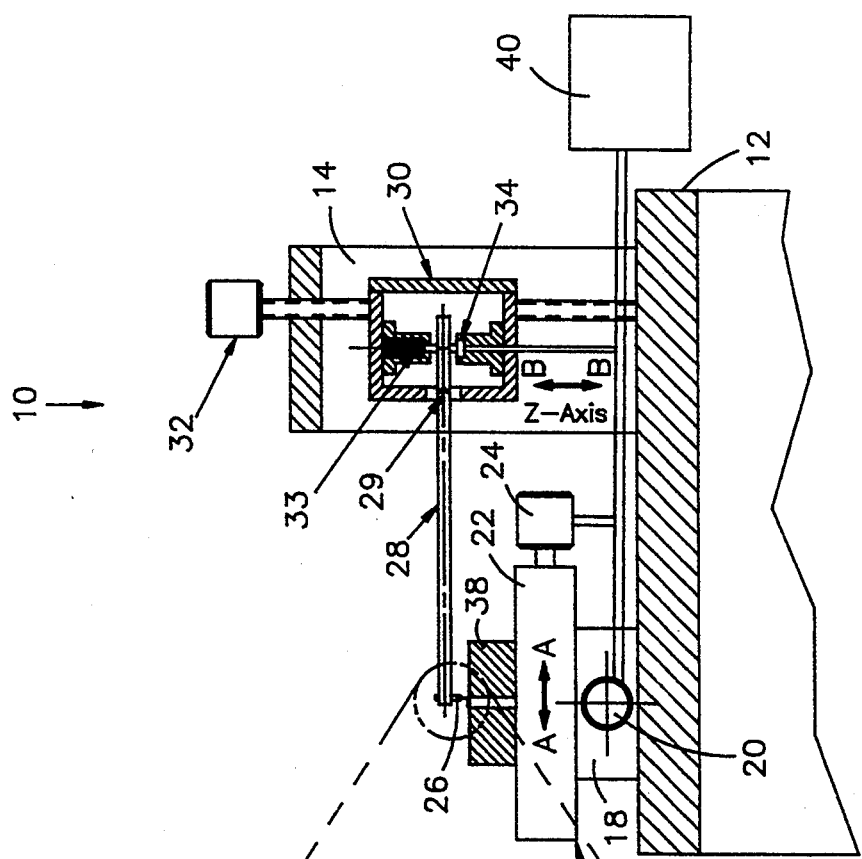
FIGS. 2 is a side view of a nondestructive test apparatus of the present invention.

FIG. 2 is the side view of a nondestructive testing apparatus 10 according to the present invention. The testing apparatus 10 comprises a support base 12 which supports a Z-axis frame 14 and a positioning bench 16 which comprises an X-adjustment bench 18 driven by an X-axis stepping motor 20 to move along an X-axis perpendicular to the surface of the paper and a Y-adjustment bench 22 which is driven by an Y-axis stepping motor 24 to move along an Y-axis parallel to the line A—A. The X-axis stepping motor 20 and the Y-axis stepping motor 24 can be controlled through the command of a computer such that the distance of movement along the X-axis (perpendicular to the paper) and the Y axis (parallel to line A—A) are within the accuracy of one micron.

A test head 26 is connected to the Z-axis box 30 via a test arm 28. The test arm 28 is pivotally connected through a pivot 29 to a Z-axis box 30 which is driven by a Z-axis stepping motor 32 to move along the Z-axis parallel to the line B—B. The Z-axis box further has a spring 33 directly contacting and asserting a downward force to the test arm 28. Right under the test arm 28 below the spring 33, the Z-axis box 30 further has a load cell 34 to measure the pressure where the test head assert upon an inner lead 44 of TAB tape which is placed on the top surface of a testing bench 38 support and controlled by the X-axis bench 18 and Y-axis bench 22.

The X-axis stepping motor 20, the Y-axis stepping motor 24, the Z-axis stepping motor 32 and the load cell 34 are all electrically connected to and controlled by a test computer 40.

Figure 3:
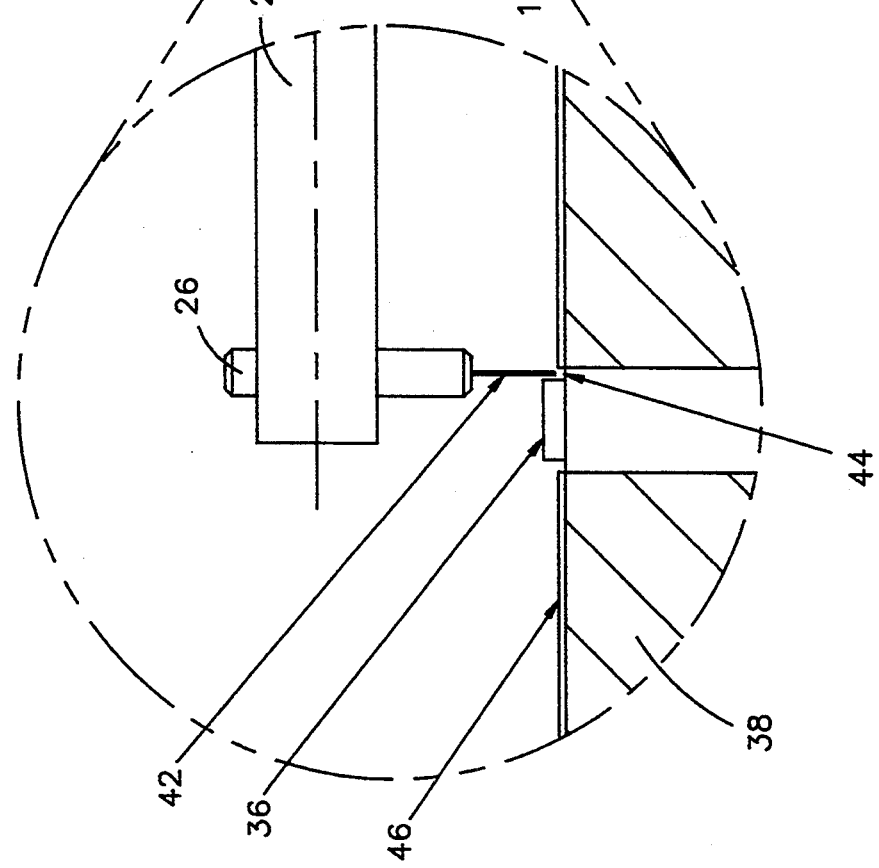
FIG. 3 is a side view of a nondestructive testing head according to the present invention.

FIG. 3 is a partially exploded side view of the test head 26 which further comprises a fine elongated straight test pin 42. The fine elongated straight test pin 42 extends downwardly to a very close distance near the inner lead 44 of TAB tape. Controlled by the test computer 40 through adjusting the position of the X-adjustment bench 18 and the Y-adjustment bench 22 driven by the stepping motors, the test pin 42 is positioned to be right above the inner lead 44 of TAB tape which is an extension of the TAB tape 46 on the surface of the IC chip 36. The Z-axis stepping motor is commanded by the test computer 40 to lower the test arm 28 and the test pin 42 to assert a certain amount of pressing force to the inner lead 44 of TAB tape. The asserted force is measured by the load cell 34 to determine the distance that the Z-axis box is to be downward adjusted such that a right amount of force is applied to the inner lead 44 for carrying out the nondestructive test. When the load cell 34 measures a pre-defined downward force, i.e., 20 grams, the test computer 40 sends a command to the Z-axis stepping motor 32 to stop the downward motion. A determination is then made of whether the bonding strength of the inner lead 44 has passed the nondestructive test.

To conduct the nondestructive testing of all the bonding on an IC chip, a preferred method is to preload a control program to the test computer 40. The control program then enables the test computer 40 to control the sequence and movement of the X-axis stepping motor 20 and the Y-axis stepping motor 24 to sequentially move the X-adjustment bench 18 and the Y-adjustment bench 22 such that the fine elongated straight test pin 42 are precisely positioned above each inner lead for testing. The test computer 40 is further enabled by the control program to activate the Z-axis stepping motor 32 to drive the Z-axis box 30 to assert a a predefined pressing force upon each test area. The test results at each test location are further recorded and stored in the test computer 40 for further process.

In one example of the preferred embodiment, the test head 26 is made from a material of stainless steel SS-304 and test pin 42 is made from tungsten. The diameter of the pin is about 0.1 millimeter and the length is about three millimeters. The nondestructive testing apparatus can test the bonding strength up to 46 grams by lowering the Z-axis box by a distance of 1.3 millimeters.

Figure 4A:
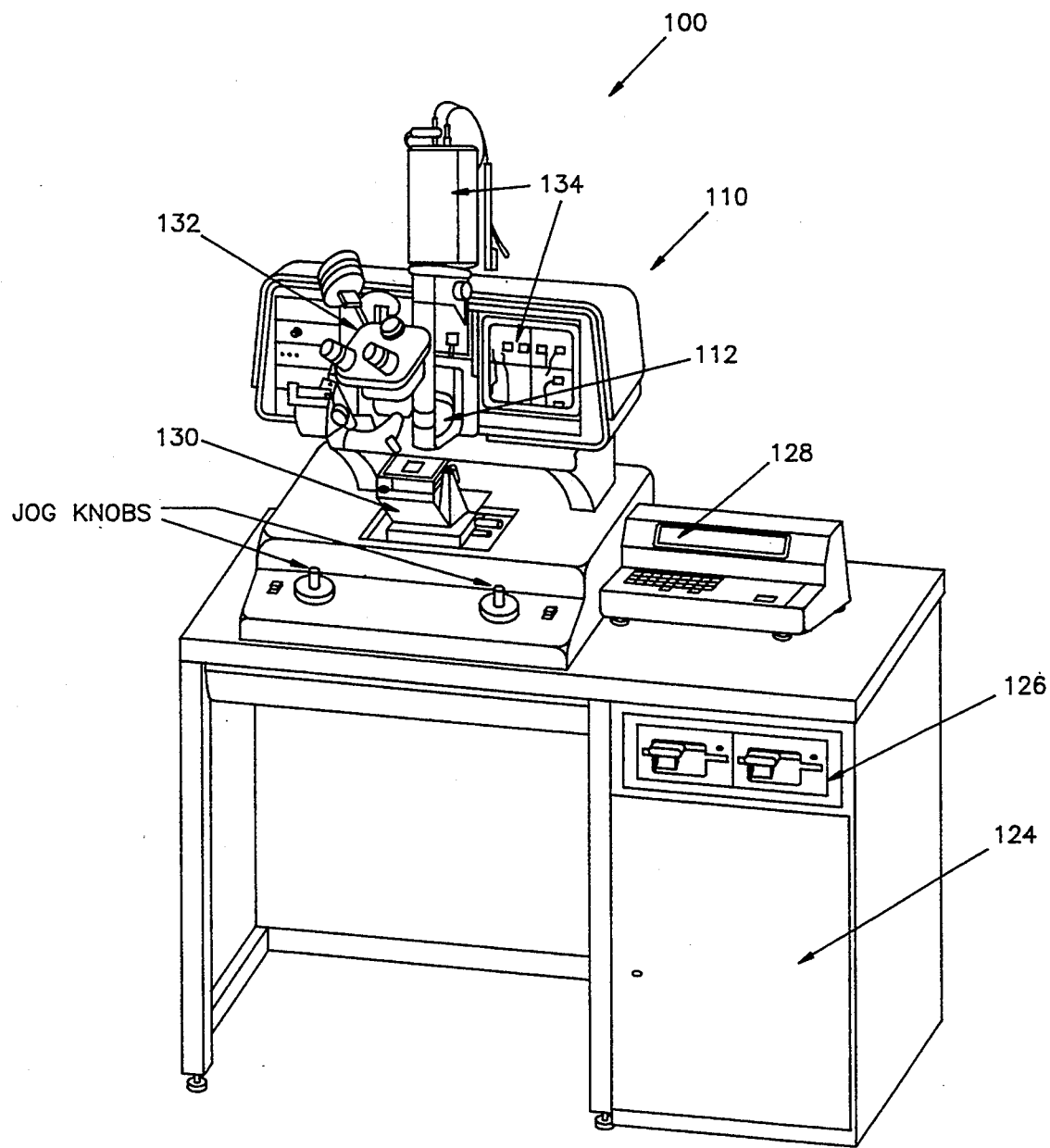
FIG. 4A is a perspective view of an alternative preferred embodiment of a nondestructive testing apparatus according to the present invention.
Figure 4B:
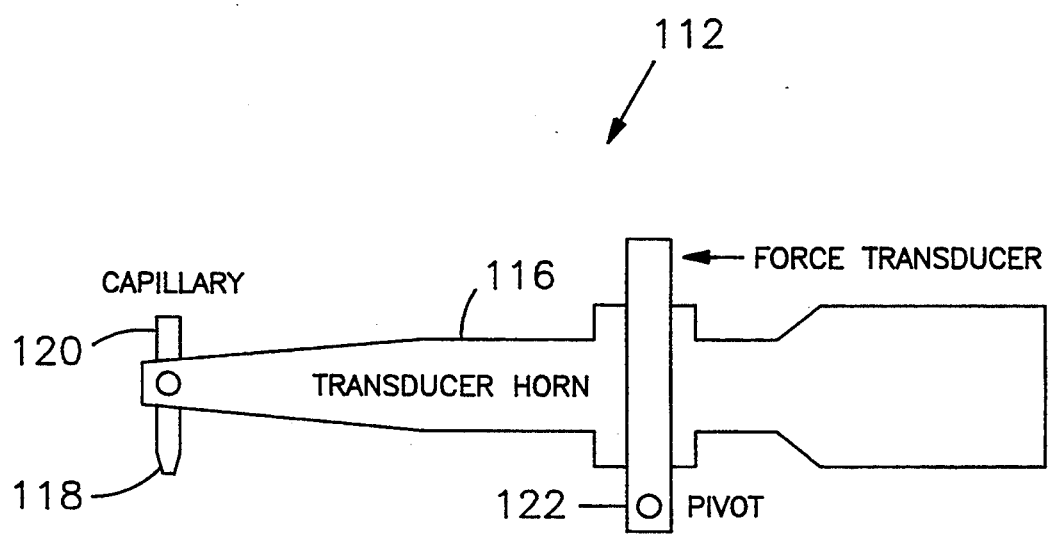
FIG. 4B is a side view of a test pin for the nondestructive testing apparatus of FIG. 4A.

FIG. 4A shows an alternate embodiment of the present invention wherein a nondestructive testing machine 100 is constructed by use a wire bonding machine 110 such as a Hughes 2460-III single head bonding machine. The capillary 120 which is attached to the transducer horn 116 (FIG. 4B) of the wire bonding head 112 (FIG. 4A) is replaced by a test head 26 and a test pin 42 (FIG. 3). Alternatively, as shown in FIG. 4B, transducer horn 116 is attached to the bonding head 112. A fine elongated straight test pin 118 is constructed identical to the test pin 42 except that it is configured such that it is adaptable to replace the capillary 120. A nondestrictive pressing force is applied to the test pin 118 by asserting the force against a pivot 122. The wire bonding machine 110 has a computer 124 to control the non-destructive test. The computer 124 includes two disk drives 126 and a keyboard/display 128. The positions of the leads to be tested are loaded into the computer 124 which then controls the movement of a X-Y table 130.

The existing function of the wire bonding machine 110 including the position adjustment and the elevation adjustment of the test head can then be used to carry out the nondestructive test similar to that performed by the testing apparatus 10. The wire-bonding machine further includes a microscope 132 and a view system 134 which may be used to inspect the results of the tests.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

We claim:

1. An apparatus for non-destructively testing the attachment strength of a first object attached to a second object at an attachment point comprising:
   a force asserting means including a fine elongated straight testing pin for asserting a controlled amount of pressing force against said first object near said attachment point thus urging said first object to tear away from said second object; and
   a control means for controlling and positioning said fine elongated straight testing pin to apply said controlled amount of pressing force.

2. The apparatus, for non-destructively testing the attachment strength as set forth in claim 1 further comprising:
   a force measurement means to measure said amount of pressing force applied against said first object.

3. An apparatus for non-destructively and individually testing the attachment strength of an electric wire to an integrated circuit (IC) dice comprising:
   a force asserting means including a fine elongated straight testing pin for asserting a controlled amount of pressing force against said electric wire near said IC dice thus urging said electric wire to tear away from said IC dice; and
   a control means for controlling and positioning said fine elongated straight testing pin to apply said controlled amount of pressing force to said electric wire.

4. An apparatus for non-destructively and individually testing the attachment strength of an electric wire to an integrated circuit (IC) dice comprising:
   a force asserting means including a fine elongated straight testing pin for asserting a controlled amount of pressing force against said electric wire near said IC dice thus urging said electric wire to tear away from said IC dice; and
   a control means including a testing arm connecting to said fine elongated straight testing pin for controlling and positioning said fine elongated straight testing pin to apply said controlled amount of pressing force to said electric wire;
   the control means further comprising a force measurement means for measuring said amount of pressing force applied to said electric wire; and
   the control means further comprising a positioning means which includes a plurality of stepping motors for adjusting the position of said testing arm.

5. A test system for non-destructively and individually testing the attachment strength of electric wires each connected to a corresponding input/output (I/O) port in an integrated circuit (IC) dice comprising:
   a test bench for placing said integrated circuit dice thereon;
   a force asserting means including a fine elongated straight testing pin for asserting a controlled amount of pressing force against each of said electric wires near said corresponding I/O ports on said IC dice thus urging said electric wires to tear away from said IC dice;
   a control means including a testing arm connecting to said fine elongated straight testing pin for controlling and positioning said fine elongated straight testing pin to apply said controlled amount of pressing force to each of said electric wires;
   the control means further comprising a force measurement means for measuring said amount of pressing force applied to each of said electric wires;
   the control means further comprising a positioning means which includes a plurality of stepping motors for adjusting the position of said testing arm; and
   a test computer connected to the control means for controlling the control means.

6. The test system for non-destructively and individually testing the attachment strength as set forth in claim 5 further comprising:

a detecting means to determine if an attachment failure occurs at said I/O port on said IC dice.

7. A test system for non-destructively and individually testing the attachment strength of a plurality of electric wires each connected to a corresponding input-/output (I/O) port in an integrated circuit dice comprising:

a test bench for placing said integrated circuit dice thereon;

a force asserting means including a fine elongated straight testing pin for asserting a pressing force against each of said electric wires thus urging said electric wires to tear away from said IC dice;

a wire-bonding machine including a testing arm connected to said said force asserting means and said fine fine elongated straight testing pin;

said wire-bonding machine further including a force measuring means for measuring the amount of said pressing force;

said wire-bonding machine further including a positioning means which including a plurality of stepping motors for adjusting the position of said testing arm thus controlling the position of said fine elongated straight pin; and said wire-bonding machine further including a computer connected to said testing arm, said force measurement means, and said positioning means for controlling and positioning said testing pin in applying said pressing force to each of said electric wires.

8. A method for non-destructively and individually testing the attachment strength of a first object attached to a second object at an attachment point comprising the steps of:

(a) positioning a fine elongated straight testing pin near said attachment point;

(b) asserting a controlled amount of pressing force against said first object near said attachment point thus urging said first object to tear away from said second object; and (c) measuring aid controlled amount of force for determining if a failure occurs at said attachment point.

9. The method for non-destructively testing the attachment strength as set forth in claim 8 wherein:

said step (c) of determining if a failure occurs at said attachment point further comprises a step of inspecting the attachment point by using a microscope.

10. A method for non-destructively and individually testing the attachment strength of an electric wire to an integrated circuit (IC) dice comprising the steps of:

(a) positioning a fine elongated straight test pin near said electric wire attached to said IC dice;

(b) utilizing said fine elongated straight test pin for asserting a controlled amount of pressing force against said electric wire thus urging said electric wire to tear away from said IC dice; and (c) measuring said pressing force for determining if a failure occurs at said attachment point.

11. The method for non-destructively and individually testing the attachment strength as set forth in claim 10 wherein:

said step (a) further comprises the step of utilizing a plurality of stepping motors for positioning said fine elongated straight test pin near said electric wire attached to said IC dice.

12. A method for non-destructively and individually testing the attachment strength of a plurality of electric wires each connected to a corresponding input/output (I/O) port in an integrated circuit (IC) dice comprising the steps of:

(a) placing said integrated circuit dice on a test bench;

(b) utilizing a plurality of stepping motors for positioning a fine elongated straight test pin near one of said electric wires connected to said corresponding I/O port;

(c) utilizing said fine elongated straight test pin for asserting a controlled amount of pressing force against said electric wire thus urging said electric wire to tear away from said IC dice;

(d) measuring said pressing force for determining if a failure occurs at said I/O port; and (e) repeating steps (a) to (d) sequentially for each of said electric wires.

13. A method for non-destructively and individually testing the attachment strength of a plurality of electric wires each connected to a corresponding input/output (I/O) port in an integrated circuit (IC) dice comprising the steps of:

(a) placing said integrated circuit dice on a test bench;

(b) utilizing a wire-bonding machine for positioning a fine elongated straight test pin near one of said electric wires connected to said corresponding I/O port;

(c) utilizing said wire-bonding machine for controlling said fine elongated straight test pin to assert a controlled amount of pressing force against said electric wire thus urging said electric wire to tear away from said IC dice;

(d) measuring said pressing force for determining if a failure occurs at said I/O port; and (e) repeating steps (a) to (d) sequentially for each of said electric wires.

* * * * *